United States Patent [19]

DeHaan

[11] Patent Number: 4,566,467

[45] Date of Patent: Jan. 28, 1986

[54] ELECTRICAL CONNECTION BETWEEN COILED LEAD CONDUCTOR AND LEAD TIP ELECTRODE

[75] Inventor: Abel DeHaan, Pembroke Pines, Fla.

[73] Assignee: Cordis Corporation, Miami, Fla.

[21] Appl. No.: 622,669

[22] Filed: Jun. 20, 1984

[51] Int. Cl.⁴ ............................................. A61N 1/04
[52] U.S. Cl. .................................. 128/784; 128/419 P
[58] Field of Search ............... 128/783, 784, 785, 786, 128/419 P

[56] References Cited

U.S. PATENT DOCUMENTS

| | | | |
|---|---|---|---|
| 3,801,954 | 4/1974 | Dorrell | 339/90 R |
| 3,871,382 | 3/1975 | Mann | 128/419 P |
| 3,890,977 | 6/1977 | Wilson | 128/418 |
| 3,995,964 | 12/1976 | DeGroef | 403/272 |
| 4,026,303 | 5/1977 | Babotai | 128/418 |
| 4,030,508 | 6/1977 | Thalen | 128/418 |
| 4,236,529 | 12/1981 | Little | 128/786 |
| 4,237,609 | 12/1980 | Clabburn et al. | 29/859 |
| 4,258,725 | 3/1981 | O'Neill | 128/419 P |
| 4,280,511 | 7/1981 | O'Neill | 128/784 |
| 4,384,404 | 5/1983 | Watine | 29/871 |
| 4,432,377 | 2/1984 | Dickhudt | 128/786 |

FOREIGN PATENT DOCUMENTS 3007307 7/1981 Fed. Rep. of Germany ... 128/419 P
3023191A1 12/1981 Fed. Rep. of Germany.

*Primary Examiner*—William E. Kamm
*Attorney, Agent, or Firm*—Henry W. Collins; Thomas R. Vigil

[57] ABSTRACT

The electrical connection of a tip electrode assembly to a pacing lead is effected by: providing bared end coils of a coiled conductor of the pacing lead; positioning the shank of a tip electrode adjacent a distal end of the bared end coils, the coils having a predetermined inner diameter and a predetermined outer diameter; positioning a conductive sleeve between the distal end of the bared end coils and the shank, the sleeve having a predetermined initial diameter greater than the outer diameter of the coils; positioning the bared end coils around the shank and the sleeve around the shank and bared end coils; and causing the sleeve to engage and force the bared end coils against the shank with the sleeve then having a smaller inner diameter.

40 Claims, 7 Drawing Figures

ELECTRICAL CONNECTION BETWEEN COILED LEAD CONDUCTOR AND LEAD TIP ELECTRODE

BACKGROUND OF THE INVENTION

1. Field of the Invention

The present invention relates to a method for connecting a tip electrode assembly to a pacing lead coiled wire conductor. The tip electrode includes a head and a shank and the distal end of the coiled wire conductor is positioned around the shank and connected thereto by a conductive sleeve. In one embodiment, the conductive sleeve is made of a transitional temperature activated mechanical memory metal so that when the sleeve is heated, it shrinks around the coiled conductor and shank to mechanically and electrically connect the coiled conductor to the shank with a permanent low-impedance conductive joint between them.

2. Description of the Prior Art

Heretofore, various methods for joining or otherwise coupling electrical conductors and/or components have been proposed. Examples of such previously proposed methods are disclosed in the U.S. patents and the German patent publications hereinafter referred to.

The Wilson U.S. Pat. No. 3,890,977 discloses a kinetic memory electrode which is adapted to be inserted into the body and anchored into a desired organ or tissue within the body. The electrode comprises a catheter having a rod made of a transitional temperature activated mechanical memory material incorporated into the tip portion of the catheter. When the electrode is inserted into the body and positioned in the desired organ or structure in the body, it is heated above its transitional temperature thereby returning to its original annealed anchoring or proper locating shape.

The DeGroef U.S. Pat. No. 3,995,964 discloses a heat recoverable article comprising a heat-shrinkable tube made, for example, of polymeric or elastomeric materials, a coaxial solder ring insert positioned against the interior wall of the tube and in a central region of the tube. The tube surrounds a spacer which divides the central region of the tube into at least two compartments. The ends of electrical conductors are inserted into each of the two compartments formed by the spacer so that when the assembly is heated, the heat causes the tube to shrink and the solder to melt and flow to wet and bond the ends of the electrical conductors together.

The Babotai U.S. Pat. No. 4,026,303 discloses an endocardial pacing electrode comprising a spiral conductor which extends the length of the catheter and which terminates at the distal end of the catheter. A second spiral, or helical, coil conductor is positioned surrounding the first conductor and is in close electrical contact therewith, both conductors being tightly encased by a catheter tube. The second coil conductor extends outside of the catheter tube to form a spiral and then turns and coils back through the center of the first coil conductor. The portion of the second coil conductor which extends through the center of the first coil conductor is soldered or otherwise connected to the first conductor to ensure electrical contact therewith.

The Thalen U.S. Pat. No. 4,030,508 discloses a low output electrode for cardiac pacing comprising an outer casing, a helical conduction lead within the casing, and a conducting element positioned at the distal end of the casing in electrical contact with the distal end of the helical conduction lead. The conducting element includes a tubular portion, which envelopes the distal end of the conduction lead and provides electrical contact therewith, and a conductive tip portion which extends axially to the far distal tip of the conducting element where it is brought to the surface with an annular form.

The Clabburn et al U.S. Pat. No. 4,237,609 discloses a heat recoverable connector assembly comprising a split cylindrical hollow tube formed from a pre-conditioned beta-brass alloy. The tube is held in a radially expanded state by a body comprising a wedge of fusible material interposed in the break in the circumference of the tube, the fusible material being, for example, polystyrene. The split tube is positioned within a fusible insert which is positioned within a heat-recoverable sleeve, the split tube being held in a radially expanded state by the fusible wedge. When a mineral insulated cable having a copper sheath, for example, is inserted into the split tube and the assembly is heated, the split tube is recovered into tight and gripping engagement with the copper sheath of the cable and the fusible insert melts and flows so as to completely encase the cable and the split tube to form a moisture-proof seal.

The O'Neill U.S. Pat. No. 4,280,511 discloses a ring electrode for a pacing lead where the ring electrode is secured to a conductor by a soft, metal disposed in a slit in the insulation over the conductor coil. A split or hole is punched into the insulation before or after the insulation is pulled over the coiled conductor. A silver ball or wire or other similar soft metal is placed in the slit or hole. A ring is slid over the insulation and centered over the soft metal, and the ring is swaged to the diameter of the insulation so that the soft metal is pressed between the ring electrode and the coiled conductor resulting in a mechanically crimped joint.

The Watine U.S. Pat. No. 4,384,404 discloses a heat recoverable article and method of connecting two electrical conductors, the heat recoverable article comprising an outer heat-shrinkable sleeve made of cross-linked polymeric materials and having at least one open end. A solder ring is positioned within the outer sleeve and remote from the open end, and an inner sleeve made of an infusible heat-shrinkable material is positioned in the area between the open end of the outer sleeve and the solder ring. The outer surface of the inner sleeve is spaced from the inner surface of the outer sleeve in order to provide a passage for receiving a first electrical conductor therebetween. A second electrical conductor is inserted into the outer sleeve but not into the passage created between the outer sleeve and the inner sleeve, and the article is heated to cause shrinkage of the outer sleeve to cause the solder to melt whereby an electrical connection is created between the first and second electrical conductors.

The Dickhudt U.S. Pat. No. 4,432,377 discloses a biomedical lead with a ring electrode and method of making same, the lead comprising a barrel-shaped ring electrode with the rings of the barrel embedded into the lead casing material. A cylindrical flange is positioned within the bore of the ring electrode and contacts the lead conductor. The lead and electrode are formed by placing the lead in a press with the electrode positioned between a pair of collets with elliptical working surfaces. The lead casing and conductor pass through the axial bore of the collets, and force the collets together to shape the electrode and to force the ends of the ring into the casing and the flange into contact with the lead conductor.

The Melton et al German published patent application No. DE3007307-A1 discloses two conductors joined by a heat activated nickel/titanium sleeve.

The Karr German published patent application No. DE3023191-A1 is of general interest and discloses an electrode for a heart pacemaker, comprising a spiral tip electrode having an elongate shank which is inserted into a helical coiled conductor.

As will be described in greater detail hereinafter, the method of the present invention for connecting a tip electrode to a coiled conductor in a pacing lead differs from the various methods previously proposed for coupling an electrical conductor to an electrode by providing for the compression swaging or shrinking of a metal sleeve around a conductor coiled around a shank of a tip electrode. The compression is achieved by swaging the metal sleeve or by heating the metal sleeve which will shrink upon heating thereof to force the coiled conductor into the shank to provide a low-impedance conductive joint between the shank and the coiled conductor.

SUMMARY OF THE INVENTION

According to the present invention, there is provided a method for manufacturing a tip electrode assembly for a pacing lead including the steps of providing bared end coils of a coiled conductor of the pacing lead; forming a shank of a tip electrode with at least two circumferentially spaced, axially extending sharp edges; positioning the shank of the tip electrode adjacent a distal end of said bared end coils; positioning a conductive sleeve made of a transitional, temperature activated, mechanical memory metal material between the distal end of the bared end coils and the shank, said sleeve being formed to have a predetermined initial inner diameter greater than an outer diameter of the coils; positioning the bared end coils around the shank and the sleeve around the bared end coils surrounding the shank; and changing the temperature of the sleeve made of the transitional, temperature activated, mechanical memory metal material thereby to shrink the sleeve and force the bared end coils into embedded engagement with the sharp shank edges as the diameter of the sleeve is shrunk to effect radially inward movement of the coils into the shank edges to form a substantially low impedance, oxide-free and gas-tight electrical connection between the coils and the shank.

Further according to the invention there is provided a tip electrode assembly for a pacing lead made according to the method described above comprising a tip electrode having a head and a shank extending behind the head and with the shank having at least two circumferentially spaced axially extending sharp edges. A coiled conductor having bared end coils at a distal end of the coiled conductor is positioned around the shank and a conductive sleeve made of a transitional, temperature activated, mechanical memory metal material is positioned around the bared end coils and the shank. The diameter of the sleeve is alterable by a change in temperature of the sleeve and the sleeve initially has a predetermined inner diameter greater than an outer diameter of the coils for enabling the sleeve to be axially moved into co-axial relation and in radial alignment with the sharp edges of the shank. Upon changing the temperature of the sleeve, the sleeve is caused to shrink around and press against the bared end coils to force the bared end coils against the sharp edges of the shank in embedded engagement therewith thereby to form a substantially low impedance, oxide-free and gas-tight electrical connection between the shank and the coils.

DESCRIPTION OF THE PREFERRED EMBODIMENT

Figure 1:
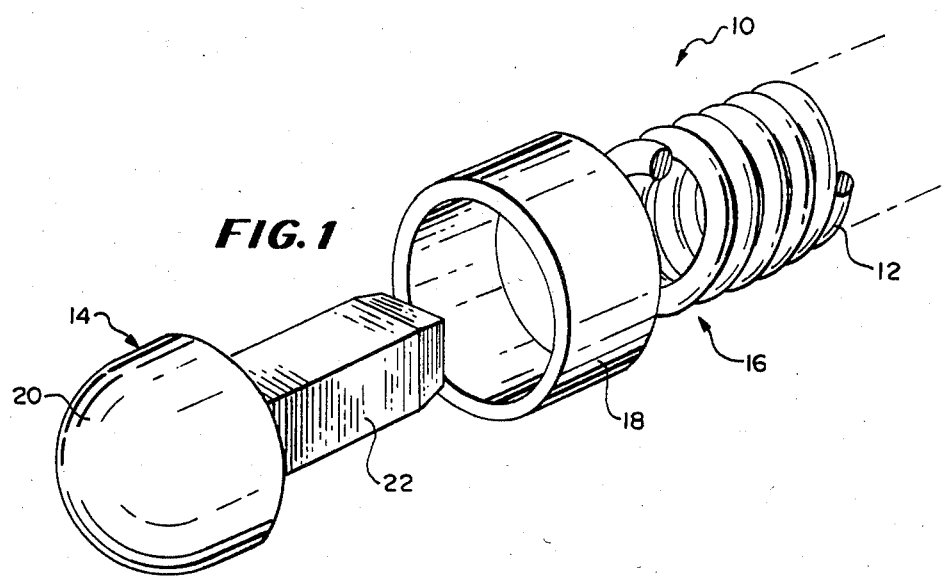
FIG. 1 is an exploded view of a tip electrode assembly constructed in accordance with the teachings of the present invention.
Figure 2:
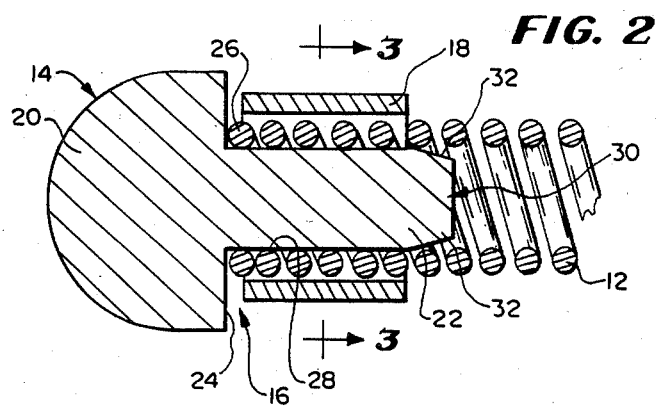
FIG. 2 is an axial sectional view of the tip electrode assembly.

Referring now to FIG. 1, there is illustrated therein, a tip electrode assembly 10 for a pacing lead which is constructed according to the teachings of the present invention. The tip electrode assembly 10 includes a coiled wire conductor 12, and a conductive tip electrode 14 which is inserted into and positioned within bared distal end coils 16 of the coiled wire conductor 12. The tip electrode assembly 10 further includes a conductive sleeve 18 which is positioned around the bared distal end coils 16 of the coiled wire conductor 12 and around the tip electrode 14.

The conductive tip electrode 14 is made of an electrically conductive material, preferably titanium, and comprises a head 20 and a shank 22, the shank 22 being square in cross-section. The shank 22 of the tip electrode 14 is positioned within the bared distal end coils 16 of the coiled wire conductor 12 so that a shoulder 24 of the head 20 is adjacent to and bears against an outer coil 26 of the coils 16.

Since a tight, zero tolerance fit is desired between the shank 22 and an inner circumference 28 of the bared distal end coils 16, the proximal end 30 of the shank 22 is provided with a chamfer or bevel edge 32 in order to provide ease of insertion of the shank 22 into the bared distal end coils 16 of the coiled wire conductor 12.

Figure 5:
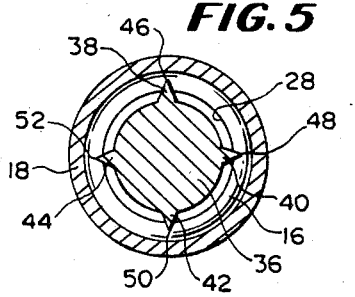
FIG. 5 is a transverse sectional view, similar to the view shown in FIG. 3, of another tip electrode assembly where a shank of a tip electrode of the assembly is circular in cross section and has axially extending ribs thereon.

Alternatively and as provided in another embodiment of the present invention shown in FIG. 5, a tip electrode can be provided with a shank 36 which is circular in cross-section and which has four elongate ribs 38, 40, 42 and 44 formed along the length of the shank 36. Each of the elongate ribs 38, 40, 42 and 44 has a sharp outer edge 46, 48, 50 and 52, respectively, which extends axially of the axis of the shank 36.

Figure 3:
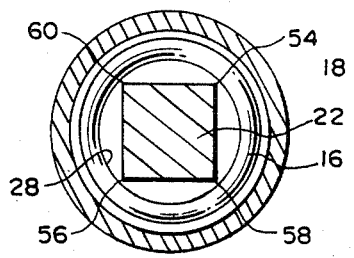
FIG. 3 is a transverse sectional view of the tip electrode assembly shown in FIG. 2 and is taken along line 3—3 of FIG. 2.

Referring back now to FIG. 3, the inner diameter of the distal end coils 16 of the conductor 12 is formed to be approximately equal to the diagonal measurement between two opposite corner edges 54, 56 or 58, 60 of the shank 22. In one embodiment the inner diameter of the bared distal end coils 16 is preferably 0.029 inch and the diagonal measurement between the two opposite corner edges 54, 56 or 58, 60 of the shank 22 is preferably 0.028 inch so that a tight, zero tolerance fit is provided therebetween. Similarly, the diagonal measurement between, for example, two opposite sharp outer edges 46, 50 of the elongate ribs 38, 42, respectively, of the shank 36 (FIG. 5) can also be 0.029 inch. Each of the elongate ribs 38, 42, as well as the elongate ribs 40, 44 extends radially outwardly 0.005 inch from the cylindrical shank 36. It is to be appreciated that the conductor 12 is made of a metallic material which is harder than titanium, and is preferably elgiloy.

A tight, zero tolerance fit is also provided between the sleeve 18 and the bared distal end coils 16 of the coiled wire conductor 12 by initially preforming the conductive sleeve 18 so that the preformed inner diameter of the sleeve 18 is approximately equal to a predetermined outer diameter of the distal end coils 16 of the conductor 12. In one embodiment, the predetermined inner diameter of the sleeve 18 is preferably 0.040 inch, and the predetermined outer diameter of the distal end coils 16 of the conductor 12 is preferably 0.039 inch, thus providing a zero tolerance fit therebetween.

The bared distal end coils 16 provide an electrically conductive inner circumferential surface 28 and such bared distal end coils 16 of the conductor 12 are in direct electrical contact with the shank 22. Further, the length of the sleeve 18, the length of the bared distal end coils 16 of the coiled wire conductor 12, and the length of the shank 22 of the tip electrode 14 are all approximately equal to each other, each being approximately 0.100 inch long, so that the shank 22 is in direct electrical contact with the entire length of the inner circumferential surface 28 of the bared distal end coils 16.

In a preferred embodiment of the present invention, the sleeve 18 is made of a transitional temperature activated mechanical memory metal material, preferably a nickel titanium alloy such as Nitinol, having an upper transitional temperature below 50° F. In this embodiment, the sleeve 18 is first preformed having an inner diameter which is less than the predetermined outer diameter of the bared distal end coils 16 of the coiled wire conductor 12, the preformed inner diameter of the sleeve 18 being 0.037 inch The sleeve 18, having a preformed inner diameter of 0.037 inch, is then annealed and subsequently reformed to a diameter which is greater than the predetermined outer diameter of the bared distal end coils 16, preferably reformed to a diameter of 0.040 inch, and accordingly, greater than its preformed inner diameter of 0.037 inch, so that the sleeve 18 can be positioned around the distal end coils 16 of the conductor 12 in a tight-fitting manner.

According to the teachings of the present invention, after the sleeve 18, reformed to have an inner diameter of 0.040 inch, is positioned around the bared distal end coils 16 of the coiled wire conductor 12 which has an outer diameter of 0.039 inch, the tip electrode assembly 10 is allowed to warm up to room temperature, the transition temperature of the nickel titanium alloy from which the sleeve 18 is made. As the sleeve 18 is heated, it returns to its initially preformed diameter of 0.037 inch causing the sleeve 18 to bear against the bared distal end coils 16 of the conductor 12 in order to urge the inner circumferential surface 28 of the bared distal end coils 16 against the shank 22 of the tip electrode 14.

Figure 4:
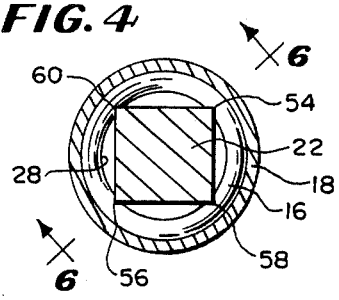
FIG. 4 is a transverse sectional view of the tip electrode assembly shown in FIG. 6, similar to the view shown in FIG. 3, after the diameter of a conductive sleeve thereof has been reduced to force same against a coil around a shank of a tip electrode of the assembly, and is taken along line 4—4 of FIG. 6.
Figure 6:
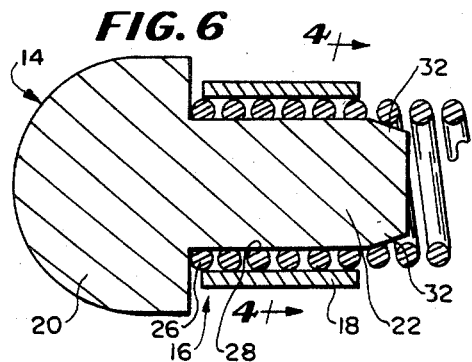
FIG. 6 is an axial sectional view of the tip electrode assembly, similar to the view shown in FIG. 2, but after the diameter of the conductive sleeve has been reduced and is taken along line 6—6 of FIG. 4.

As further illustrated in FIGS. 4 and 5, since the conductor 12 is made of elgiloy, which is a harder metal than titanium, the inner circumferential surface 28 of the distal end coils 16 of the conductor 12 "bite" into the corner edges 54, 56, 58 and 60 of the shank 22 (FIG. 4). Likewise, the inner circumferential surface 28 of the bared distal end coils 16 of the conductor 12 "bite" into the sharp outer edges 46, 48, 50 and 52 of the four elongate ribs 38, 40, 42 and 44, respectively, of the shank 36 (FIG. 5). Accordingly, the edges of the titanium shank 22 (FIG. 4), or the rib edges 46, 48, 50 and 52 (FIG. 5), are broken by the inner circumferential surface 28 of the bared distal end coils 16 of the coiled wire conductor 12. This action causes the bared distal end coils 16 to break through the oxide layer on the titanium shank 22 (FIG. 4), or the titanium shank 36 (FIG. 5), allowing the metal of the bared distal end coils 16 to come into direct contact with the titanium metal of the titanium shank 22, or the titanium shank 36, thereby to form a permanent low impedance, oxide-free and gas-tight electrically conductive joint therebetween.

Figure 7:
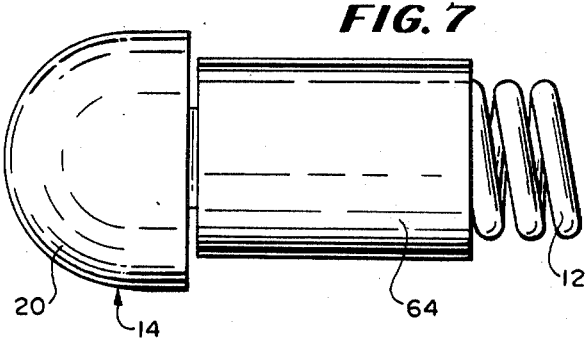
FIG. 7 is a side view of still another tip electrode assembly constructed according to the teachings of the present invention in which a conductive sleeve of the assembly is swaged to reduce the inner diameter thereof and force same against a coil around a shank of a tip electrode of the assembly.

In another embodiment of the present invention shown in FIG. 7, the method of connecting the shank 22 (FIG. 4), or the shank 36 (FIG. 5), of the tip electrode 14 to the bared distal end coils 16 of the coiled wire conductor 12, can be similarly achieved by positioning a sleeve 64 made of, for example, stainless steel, around the bared distal end coils 16 surrounding the shank 22 or 36. The sleeve 64 also has an inner diameter which is approximately equal to the outer diameter of the bared distal end coils 16 in order to provide a tight, zero tolerance fit therebetween. The sleeve 64 initially has a length at least equal to the length of the shank 22 or the shank 36. In one embodiment, the inner diameter of the sleeve 64 is 0.040 inch, the outer diameter of the bared distal end coils 16 is 0.039 inch, and the length of the sleeve 64 is 0.100 inch.

The inner diameter of the sleeve 64 is reduced to a diameter less than the outer diameter of the distal end coils 16 of the conductor 12 by rotary swaging of the sleeve 64 around the bared distal end coils 16 surrounding the shank 22 or 36. The rotary swaging of the sleeve 64 around the bared distal end coils 16 reduces the inner diameter of the sleeve 64 to approximately 0.037 inch in order to urge the sleeve 64 against the bared distal end coils 16 of the conductor 12 thereby causing the inner circumferential surface 28 of the bared distal end coils 16 to "bite" into the corner edges 54, 56, 58 and 60 of the shank 22 (FIG. 4) or rib edges 46–52 of the shank 36 (FIG. 5). As a result, the edges 54, 56 and 60 of the titanium shank 22 (FIG. 4), or the rib edges 46, 48, 50 and 52 of the shank 36 (FIG. 5), are broken by the inner circumferential surface 28 of the bared distal end coils 16 to engage the corners 54–60, or the rib edges 46–50, thereby to break through the oxide layers of the titanium shank 22 or 36 and to coldweld the shank 22 to the bared distal end coils 16 of the conductor 12, or to coldweld the shank 36 so the bared distal end coils 16 of the conductor 12, thereby to form a permanent, low-impedance, oxide-free and gas-tight electrically conductive joint therebetween.

It is apparent that one of the advantages of manufacturing the tip electrode assembly 10 according to the methods heretofore described, is that the conductive tip electrode 14 is connected to the conductor 12 with a permanent low-impedance conductive joint therebetween as a result of the physical properties of the sleeve 18, or the swaging of the sleeve 64, positioned around the shank 22 or 36, respectively, without the use of solder or other welding material thereby to provide an oxide-free and gas-free bond or joint.

From the foregoing description, it will be apparent that the method of manufacturing the tip electrode assembly 10 according to the teachings of the present invention has a number of advantages, some of which have been described above and others of which are inherent in the invention. Also, it will be apparent that modifications can be made to the method and tip electrode assembly formed thereby without departing from the teachings of the present invention.

Accordingly, the scope of the invention is only to be limited as necessitated by the accompanying claims.

I claim:

1. A method for manufacturing a tip electrode assembly for a pacing lead including the steps of: providing bared end coils of a coiled conductor of the pacing lead; forming a shank of a tip electrode with at least two circumferentially spaced, axially extending sharp edges; positioning the shank of the tip electrode adjacent a distal end of said bared end coils; positioning a conductive sleeve of a transitional, temperature activated, mechanical memory metal material between said distal end of said bared end coils and said shank, said sleeve being formed to have a predetermined initial inner diameter greater than an outer diameter of said coils; positioning said bared end coils around said shank and said sleeve around said bared and coils surrounding said shank; and changing the temperature of said sleeve made of the transitional, temperature activated, mechanical memory material thereby to shrink said sleeve and force said bared end coils into embedded engagement with said sharp edges as the diameter of said sleeve is shrunk to effect radially inward movement of said coils into the shank edges to form a substantially low impedance, oxide-free and gas-tight electrical connection between said coils and said shank.

2. The method of claim 1 including the step of forming said shank with a square cross-section and with a diagonal dimension of approximately 0.028 inch.

3. The method of claim 1 including the step of forming said bared end coils with an inner diameter of approximately 0.029 inch.

4. The method of claim 1 including the step of forming said bared end coils with an outer diameter almost equal to an inside diameter of said sleeve member.

5. The method of claim 4 including the step of forming said bared end coils with an outer diameter of approximating 0.039 inch.

6. The method of claim 4 including the step of forming said inside diameter of said sleeve with a dimension of approximately 0.040 inch.

7. The method of claim 1 including the step of forming said sleeve with a length almost equal to the length of said shank of said tip electrode.

8. The method of claim 7 including the step of forming said shank of said tip electrode with a length of at least 0.100 inch.

9. The method of claim 1 including the step of forming said sleeve with a length of at least 0.100 inch.

10. The method of claim 4 including the step of forming said conductive tip electrode of a metal which is harder than the metal from which said conductor bared end coils are made.

11. The method of claim 10 wherein said tip electode is made of titanium, and said coiled conductor is made of eligiloy.

12. The method of claim 1 including the step of forming said sleeve with an inner diameter of approximately 0.037 inch.

13. The method of claim 1 wherein the inner diameter of said sleeve is caused to shrink to approximately 0.037 inch.

14. The method of claim 1 wherein said transitional, temperature activated, mechanical memory metal material is formed from a nickel-titanium alloy.

15. The method of claim 14 wherein said alloy has an upper transition temperature below 50° F.

16. The method of claim 1 including the step of forming the shank round in cross-section and with at least two elongate ribs extending the length of said shank, each of said elongate rib having one of said sharp outer edges, the ribs being located opposite each other and extending axially of the axis of said shank.

17. The method of claim 16 wherein the diameter of said shank across said ribs is approximately 0.028 inch.

18. The method of claim 16 wherein said at least two elongate ribs are formed with a height above said shank of approximately 0.005 inch.

19. The method of claim 16 wherein said shank is formed with four elongate ribs extended along the length of said shank, each rib having an outer edge and said ribs being equally spaced around the circumference of said shank.

20. A tip electrode assembly for a pacing lead comprising: a tip electrode having a head and a shank extending behind said head; said shank having at least two circumferentially spaced axially extending sharp edges; a coiled conductor having bared end coils at a distal end of said coiled conductor; said bared end coils being positioned around said shank; a conductive sleeve made of a transitional, temperature activated, mechanical memory metal material and positioned around said bared end coils and said shank; the diameter of said sleeve being alterable by a change in temperature of said sleeve; said sleev initially having a predetermined inner diameter greater than an outer diameter of said coils for enabling the sleeve to be axially moved into co-axial relation and in radial alignment with said sharp edges of said shank; and upon changing the temperature of said sleeve being caused to shrink around and press against said bared end coils to force said bared end coils against said sharp edges of said shank in embedded engagement therewith thereby to form a substantially low impedance, oxide-free and gas-tight electrical connection between said shank and said coils.

21. The assembly of claim 20 wherein said shank is square in cross-section so as to form said shank with four sharp edges engageable in edgewise biting engagement with said coils.

22. The assembly of claim 21 wherein the diagonal dimension of said square in cross-section shank is almost equal to an inner diameter of said bared end coils.

23. The assembly of claim 22 wherein said diagonal dimension of said square in cross-section shank is approximately 0.028 inch.

24. The assembly of claim 19 wherein an inner diameter of said bared end coils is approximately 0.029 inch.

25. The assembly of claim 20 wherein an outer diameter of said bared end coils is almost equal to an inside diameter of said sleeve member for co-active retaining engagement therewith.

26. The assembly of claim 25 wherein said outer diameter of said bared end coils is approximately 0.039 inch and an inside diameter of said sleeve is slightly more when assembled therewith.

27. The assembly of claim 25 wherein said predetermined initial diameter of said sleeve is approximately 0.040 inch.

28. The assembly of claim 20 wherein the length of said sleeve is less than the length of said shank of said tip electrode to permit the components to be more readily assembled.

29. The assembly of claim 28 wherein said length of said shank of said tip electrode is at least 0.100 inch for supporting the bared end coils thereon.

30. The assembly of claim 28 wherein said length of said sleeve is at least 0.100 inch for engagement with the coils.

31. The assembly of claim 20 wherein said tip electrode is made of titanium.

32. The assembly of claim 20 wherein said conductor is made of elgiloy.

33. The assembly of claim 20 wherein an inner diameter of said sleeve is approximately 0.037 inch.

34. The assembly of claim 20 wherein said transitional, temperature activated, mechanical memory metal material is a nickel-titanium alloy.

35. The assembly of claim 34 wherein said alloy has an upper transitional temperature below 50° F.

36. The assembly of claim 34 where any oxide layer on the titanium alloy shank in the area of said sharp edges is broken through when said sharp edges bite into the inner circumferential surface of said end coils such that said coils come into direct contact with the titanium metal of said shank.

37. The assembly of claim 20 wherein said shank is round in cross-section and includes at least two elongate ribs formed along the length of said shsnk, each of said elongate ribs having one of said sharp edges, the ribs being located opposite each other and extending axially of the axis of said shank.

38. The assembly of claim 37 wherein said shank has a diameter across said ribs of approximately 0.028 inch.

39. The assembly of claim 38 wherein said at least two elongate ribs each have a radial dimension beyond said shank of approximately 0.005 inch.

40. The assembly of claim 38 wherein said shank includes four elongated ribs extending radially along the length of said shank, each rib having an outer edge and said ribs being equally spaced around the circumference of said shank from engaging said coils.

* * * * *